US00PP31812P2

(12) United States Plant Patent
Klemm et al.

(10) Patent No.: US PP31,812 P2
(45) Date of Patent: May 26, 2020

(54) ***PELARGONIUM* PLANT NAMED 'KLEPZ18547'**

(50) Latin Name: *Pelargonium zonale*
Varietal Denomination: KLEPZ18547

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,840

(22) Filed: Jun. 17, 2019

(51) Int. Cl.
*A01H 5/02* (2018.01)
*A01H 6/42* (2018.01)

(52) U.S. Cl.
USPC ..... Plt./330
CPC ..... *A01H 6/425* (2018.05)

(58) Field of Classification Search
USPC ..... Plt./330
CPC ..... A01H 6/425; A01H 5/02
See application file for complete search history.

*Primary Examiner* — Keith O. Robinson
(74) *Attorney, Agent, or Firm* — Barbara Campbell; Cochran Freund & Young LLC

(57) ABSTRACT

A new *pelargonium* plant particularly distinguished by dark-red flowers, strong zonation of the leaves; and a bushy and round plant habit with medium vigor, is disclosed.

1 Drawing Sheet

Genus and species: *Pelargonium zonale.*
Variety denomination: 'KLEPZ18547'.

CROSS-REFERENCE TO RELATED APPLICATIONS

A Swiss Plant Breeders Rights Application was filed on May 31, 2018, Application No. 18-3219 and a Community Plant Variety Rights application was filed on Jul. 19, 2018, File No. 2018/1826. 'KLEPZ18547' has not been made publicly available for more than one year prior to the filing date of the instant application.

BACKGROUND OF THE NEW PLANT

The present invention comprises a new and distinct variety of *pelargonium*, botanically known as *Pelargonium zonale* and hereinafter referred to by the variety name 'KLEPZ18547'. 'KLEPZ18547' originated from a hand-pollination in September 2012 in Stuttgart, Germany between the female *pelargonium* variety 'KLEPZ10238', also commercially known as SUNRISE 'XL Leon' (U.S. Plant Pat. No. 23,116) and the male *pelargonium* variety 'KLEPZ12320', also commercially known as SUNRISE 'Carlos' (unpatented).

Seeds from the hand-pollination were obtained. The seeds were sown and plants were grown for evaluation. A single plant was selected in June 2013 and subsequently named 'KLEPZ18547'. In September 2013 'KLEPZ18547' was first vegetatively propagated by vegetative cuttings. 'KLEPZ18547' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Dark-red flowers;
2. Strong zonation of the leaves; and
3. A bushy and round plant habit with medium vigor.

DESCRIPTION OF THE PHOTOGRAPH

This new *pelargonium* plant is illustrated by the accompanying photograph which shows an overall view of the plant. The photograph is of an approximately 4-month-old plant grown outdoors in Stuttgart, Germany, in July 2015. The colors shown are as true as can be reasonably obtained by conventional photographic procedures.

DESCRIPTION OF THE NEW VARIETY

The following detailed descriptions set forth the distinctive characteristics of 'KLEPZ18547'. The data which define these characteristics were collected from asexual reproductions carried out in Stuttgart, Germany. Data was collected on 19-week-old plants in Stuttgart, Germany under greenhouse conditions in May 2019. Color references are to The R.H.S. Colour Chart of The Royal Horticultural Society of London (R.H.S.), $6^{th}$ edition (2015).

Classification:
*Family.*—Geraniaceae.
*Botanical.*—*Pelargonium zonale.*
*Common.*—*Pelargonium.*
*Designation.*—'KLEPZ18547'.

Parentage:
*Female parent.*—'KLEPZ10238' (U.S. Plant Pat. No. 23,116).
*Male parent.*—'KLEPZ12320' (unpatented).

Plant:
*Form.*—Bushy and round.
*Habit.*—Upright.

*Height* (*from top of soil*).—15 cm.
*Width* (*horizontal plant diameter*).—26 cm.
*Natural flowering season*.—April to October.
*Propagation type*.—Vegetative cuttings.
*Time to produce a finished flowering plant*.—3 months.
*Time to initiate and develop roots*.—4 weeks.
*Root description*.—Fine, dense, RHS 199C.

Stems:
*Quantity of stems per plant*.—4 to 5.
*Color*.—RHS 143C.
*Surface texture*.—Moderately pubescent.
*Stem form*.—Round.
*Diameter*.—0.7 cm.
*Length*.—4 cm.
*Internode length*.—0.7 cm.
*Anthocyanin*.—Absent.

Leaves:
*Arrangement*.—Alternate.
*Shape*.—Reniform.
*Apex*.—Round.
*Base*.—Open.
*Margin*.—Crenate.
*Surface texture* (*both surfaces*).—Sparsely pubescent.
*Length*.—4.5 cm.
*Width*.—6 cm.
*Color*.—Upper surface: RHS 137B. Lower surface: RHS 143B.
*Zonation*.—Present.
*Zone conspicuousness*.—Strong.
*Zone position*.—Towards margin.
*Relative size of zone*.—Large.
*Color*.—RHS 183B.
*Petiole*.—Length: 5 cm. Diameter: 0.2 cm to 0.3 cm. Color: RHS 143B. Strength: Moderate.
*Venation pattern*.—Palmate.
*Venation color*.—Upper surface: RHS 137B. Lower surface: RHS 143C.

Inflorescence:
*Lastingness of flowers on the plant*.—6 to 8 days.
*Umbels*.—Quantity of umbels per plant: 8 to 9. Length: 5 cm. Diameter: 10 cm.
*Individual florets of the umbel*.—Quantity of florets per umbel: 30 to 35. Depth: 2 cm. Diameter: 5 cm.
*Fragrance*.—Absent.

Flower buds:
*Cluster shape*.—Round.
*Cluster size*.—Length: 1.5 cm. Width: 3 cm.
*Surface texture*.—Sparsely pubescent.
*Bud*.—Height: 0.8 cm. Width: 0.5 cm. Shape: Round. Apex: Acute. Base: Obtuse. Margin: Entire. Color: RHS 144B.

Petals:
*Quantity per flower*.—10.
*Shape*.—Spatulate.
*Apex*.—Round.
*Base*.—Obtuse.
*Margin*.—Entire.
*Length*.—2.6 cm.
*Width*.—2.4 cm.
*Surface texture* (*both surfaces*).—Smooth.
*Color of lobes*.—Upper and lower lobes: Upper surface: RHS 45B. Lower surface: RHS N34B.

Petaloids:
*Quantity per flower*.—3 to 4.
*Shape*.—Like petals but smaller, some mal-shaped and twisted.
*Apex*.—Round.
*Base*.—Obtuse.
*Margin*.—Entire.
*Length*.—2 cm.
*Width*.—0.5 cm.
*Surface texture* (*both surfaces*).—Smooth.
*Color*.—Upper surface: RHS 40A. Lower surface: RHS N34B.

Sepals:
*Number per flower*.—5.
*Shape*.—Elliptic.
*Apex*.—Acute.
*Base*.—Obtuse.
*Margin*.—Entire.
*Surface texture*.—Upper surface: Smooth. Lower surface: Sparsely pubescent.
*Color*.—Upper surface: RHS 143B. Lower surface: RHS 143A.
*Length*.—1 cm.
*Width*.—0.3 cm.

Pedicel:
*Length*.—2.5 cm.
*Diameter*.—0.1 cm.
*Color*.—RHS 144A.
*Surface texture*.—Sparsely pubescent.
*Strength*.—Moderate.

Peduncle:
*Length*.—11 cm.
*Diameter*.—4 cm.
*Color*.—RHS 144A.
*Texture*.—Sparsely pubescent.
*Strength*.—Moderate.

Reproductive organs:
*Stamens*.—Quantity per flower: 7. Anther length: 0.8 cm. Filament length: 0.2 cm. Filament color: RHS 51B. Pollen amount: Moderate. Pollen color: RHS N25A.
*Pistils*.—Number: 1. Stigma color: RHS 60A. Style length: 0.5 cm. Style color: RHS 143C. Ovary arrangement: Central. Ovary color: RHS 143C. Ovary diameter: 0.1 cm. Ovary length: 0.1 cm.

Fruit and seed set: None observed.

Disease and pest/insect resistance: None observed.

COMPARISON WITH PARENTAL LINES AND KNOWN VARIETY

'KLEPZ18547' is distinguished from its parents as described in Table 1:

TABLE 1

| Comparison with Parental Lines | | | |
|---|---|---|---|
| Characteristic | 'KLEPZ18547' | Female parent 'KLEPZ10238' | Male Parent 'KLEPZ12320' |
| Zonation conspicuousness | Strong | Absent | Weak |
| Vigor | Medium | Strong | Weak |

'KLEPZ18547' can be compared to the commercial variety SUNRISE 'Fernando', also known as 'KLEP03105' (unpatented). Differences between the two varieties are described in Table 2:

TABLE 2

| Comparison with Similar Variety | | |
|---|---|---|
| Characteristic | 'KLEPZ18547' | 'KLEP03105' |
| Flower color | Dark-red | Red |
| Vigor | Weak | Medium |

We claim:

1. A new and distinct variety of *pelargonium* plant named 'KLEPZ18547' as illustrated and described herein.

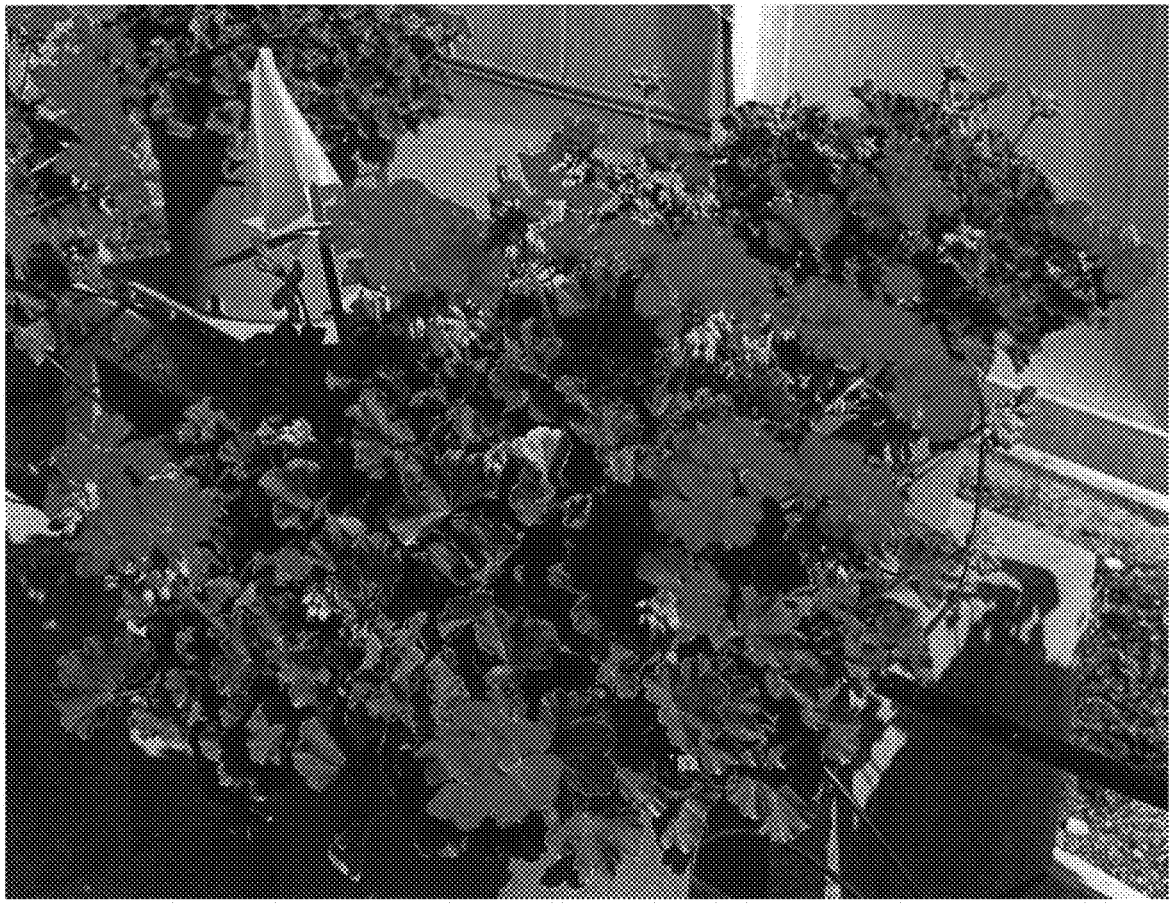

* * * * *